(12) United States Patent
Cech et al.

(10) Patent No.: US 7,338,170 B2
(45) Date of Patent: Mar. 4, 2008

(54) LENS SYSTEMS FOR VITREORETINAL SURGERY

(75) Inventors: Steven D. Cech, Aurora, OH (US); Kakarla V. Chalam, Jacksonville, FL (US); Timothy D. Edwards, Cleveland, OH (US); Gerald Kotnik, Perry, OH (US)

(73) Assignee: Volk Optical Inc., Mentor, OH (US)

( * ) Notice: Subject to any disclaimer, the term of this patent is extended or adjusted under 35 U.S.C. 154(b) by 213 days.

(21) Appl. No.: 11/251,112

(22) Filed: Oct. 14, 2005

(65) Prior Publication Data

US 2006/0244914 A1 Nov. 2, 2006

Related U.S. Application Data

(60) Provisional application No. 60/676,159, filed on Apr. 29, 2005.

(51) Int. Cl.
*A61B 3/00* (2006.01)
(52) U.S. Cl. ......................... 351/219; 351/218
(58) Field of Classification Search ......... 351/217–219
See application file for complete search history.

(56) References Cited

U.S. PATENT DOCUMENTS

| 3,950,082 | A | | 4/1976 | Volk |
|---|---|---|---|---|
| 4,002,439 | A | | 1/1977 | Volk |
| 4,050,192 | A | | 9/1977 | Volk |
| 4,149,801 | A | | 4/1979 | Volk |
| 4,640,595 | A | | 2/1987 | Volk |
| 4,710,193 | A | | 12/1987 | Volk |
| 4,913,545 | A | * | 4/1990 | Volk .......................... 351/205 |
| 5,046,836 | A | | 9/1991 | Volk |
| 5,173,723 | A | | 12/1992 | Volk |
| 5,200,773 | A | | 4/1993 | Volk |
| 5,255,025 | A | | 10/1993 | Volk |
| 5,347,326 | A | | 9/1994 | Volk |
| 5,430,506 | A | | 7/1995 | Volk |
| 5,436,680 | A | | 7/1995 | Volk |
| 5,440,458 | A | | 8/1995 | Volk |
| 5,479,222 | A | | 12/1995 | Volk |
| 5,523,810 | A | | 6/1996 | Volk |
| 5,526,074 | A | | 6/1996 | Volk |
| 5,706,073 | A | | 1/1998 | Volk |
| 5,745,212 | A | | 4/1998 | Volk |
| 5,757,464 | A | | 5/1998 | Volk |
| 5,784,147 | A | | 7/1998 | Volk |
| 5,805,269 | A | | 9/1998 | Volk |
| 5,857,475 | A | | 1/1999 | Volk |
| 5,886,812 | A | | 3/1999 | Volk |
| 5,963,301 | A | | 10/1999 | Volk |
| 5,986,801 | A | | 11/1999 | Volk |
| 6,164,779 | A | | 12/2000 | Volk |
| 6,851,808 | B2 | * | 2/2005 | Heacock ..................... 351/219 |
| 2005/0157260 | A1 | * | 7/2005 | Graham et al. ............. 351/219 |

* cited by examiner

*Primary Examiner*—Jordan M. Schwartz
(74) *Attorney, Agent, or Firm*—Dinsmore & Shohl LLP

(57) ABSTRACT

An ophthalmoscopy lens system includes a contact lens and an image forming lens. The contact lens and the image forming lens are in a spaced-apart arrangement such that an open air space exists between the contact lens and the image forming lens and the inner surfaces are exposed.

20 Claims, 5 Drawing Sheets

LENS SYSTEMS FOR VITREORETINAL SURGERY

CROSS REFERENCES TO RELATED APPLICATIONS

This application claims the benefit of U.S. Provisional Application No. 60/676,159 filed on Apr. 29, 2005, which is hereby incorporated by reference.

BACKGROUND OF THE INVENTION

1. Field of the Invention

The present invention relates to ophthalmoscopy lens systems, particularly those which may be easily sterilized without component damage or optical degradation.

2. Description of Related Art

Various ophthalmoscopy lens systems have been developed for use in the diagnosis and treatment of the eye. Many of these lens systems, particularly indirect ophthalmoscopy lens systems which create a real aerial image of structures within the eye, include a contact lens element which is placed directly on a patient's cornea. One particular type of indirect ophthalmoscopy lens system is that used for vitreoretinal surgery. Such lens systems are described, for example, in U.S. Pat. No. 5,963,301 (which is hereby incorporated by reference). Such lens systems are typically exposed to various bodily fluids during use, and therefore must be sterilized prior to each use.

Sterilization of ophthalmoscopy lens systems can be difficult and time consuming. In fact, many ophthalmoscopy lens systems can only be sterilized by specialized, time-consuming sterilization techniques, many of which will not be effective for certain microorganisms and other infectious agents. By way of example, "prions" are proteinaceous infectious agents which can cause transmissible degenerative encephalopathies such as Creutzfeldt-Jakob disease ("CJD"—a variant of which is the human version of "Mad Cow disease"). Prions tend to be more resistant to steam sterilization than conventional agents and are resistant to most sterilants typically used for sterilizing ophthalmoscopy lens systems. Recently, it has been reported that prions are susceptible to conventional autoclaving followed by a strong bleach solution or a solution of sodium hydroxide. Such a sterilization process will denature the prions. However, standard autoclaving cannot be employed with conventional ophthalmoscopy lens systems, particularly vitreoretinal lens systems such as those described in U.S. Pat. No. 5,963,301. Not only will the environment and bleach solution damage the lens element and other components, but liquid will enter the air space between the contact lens element and the imaging lens.

For example, the high-temperature, high-pressure steam environment of an autoclave is deleterious to both the contact lens element as well as the imaging forming lens. More particularly, acrylic contact lens elements, as they are typically implemented, tend to quickly haze and otherwise become non-transparent after a few cycles within a steam autoclave sterilizer. Also, glass image forming lenses interact with the steam produced by an autoclave to form hard water surface spotting. These hard water surface spots accumulate over repeated autoclave cycles and eventually render the glass lens element incompatible with effective retinal imaging.

In addition, as previously indicated, prior ophthalmoscopy lens systems are susceptible to water damage when liquid enters the air space between the contact lens element and the imaging lens. Such ophthalmoscopy lens systems include those configured such that the contact lens element and the image forming lens are in a spaced-apart sealed arrangement wherein a sealed air space is provided between the contact lens and the image forming lens. Such a lens system is described in U.S. patent application Ser. No. 10/689,568 (which is hereby incorporated by reference). After a number of steam autoclave cycles, due to the porosity of the high-temperature polymer housing and sealing members used in their construction, water in both vapor and liquid form encroach into the sealed cavity between the contact lens element and the image forming lens. This water eventually settles in sufficient quantities on the internal surfaces of the lenses to render the lens assembly incompatible with effective retinal imaging. Once water has breached into the internal cavity and has condensed on the internal lens surfaces, the internal surfaces have to be cleaned and dried before the lens can be effectively applied again. Moreover, vitrectomy lenses of this type are not well suited for disassembly and cleaning, as they require special tools to facilitate these actions.

Accordingly, there is a need for an ophthalmoscopy lens system of suitable composition and structure which may be easily sterilized without component damage or optical degradation.

SUMMARY OF THE INVENTION

The present invention provides an autoclavable and sterilent-resistant ophthalmoscopy lens system, comprising a contact lens, and at least one image forming lens element. Such a lens system may be used, for example, as an indirect ophthalmoscopy lens system for use in the diagnosis or treatment of a patient's eye. In one particular embodiment, the lens system is configured such that the contact lens and the image forming lens element are in a spaced-apart arrangement such that an open air space exists between the contact lens and the image forming lens element. More particularly, one or more openings may be provided in the frame of the lens system such that inner surfaces of the contact and image forming lenses are exposed. Of course, more than one image forming lens elements may be employed, and a compound contact lens may be used if desired.

The ophthalmoscopy lens system may further comprise a frame or housing, wherein the contact lens is removably mounted to the frame. The system may further comprise a retaining ring wherein an image forming lens element is secured within the retaining ring. In such embodiment, the frame may have posterior and anterior ends, with the contact lens mounted to the housing at the posterior end of the housing and the retaining ring mounted to the anterior end of the housing. The housing may comprise one or more openings so that the inner surfaces of the contact and image forming lenses can be exposed.

BRIEF DESCRIPTION OF THE DRAWINGS

While the specification concludes with claims particularly pointing out and distinctly claiming the present invention, the invention will be further understood from the following detailed description taken in conjunction with the accompanying drawings in which:

DETAILED DESCRIPTION

The present invention provides an ophthalmoscopy lens system, such as a lens system suitable for use during vitreoretinal surgery, which may be easily and effectively sterilized and decreasing or eliminating component damage and optical degradation. In particular, as discussed herein, lens systems according to the present invention facilitate autoclaving and subsequent drying of both surfaces of the contact and image forming lenses as a result of exposure of the interior surfaces of the lenses through openings within the frame or housing. In addition, by proper selection of the materials used to manufacture the various components of the lens system, the lens systems can be sterilized without significant damage to the components (particularly the individual lens elements) or degradation of the optical characteristics of the lens system.

Figure 1:
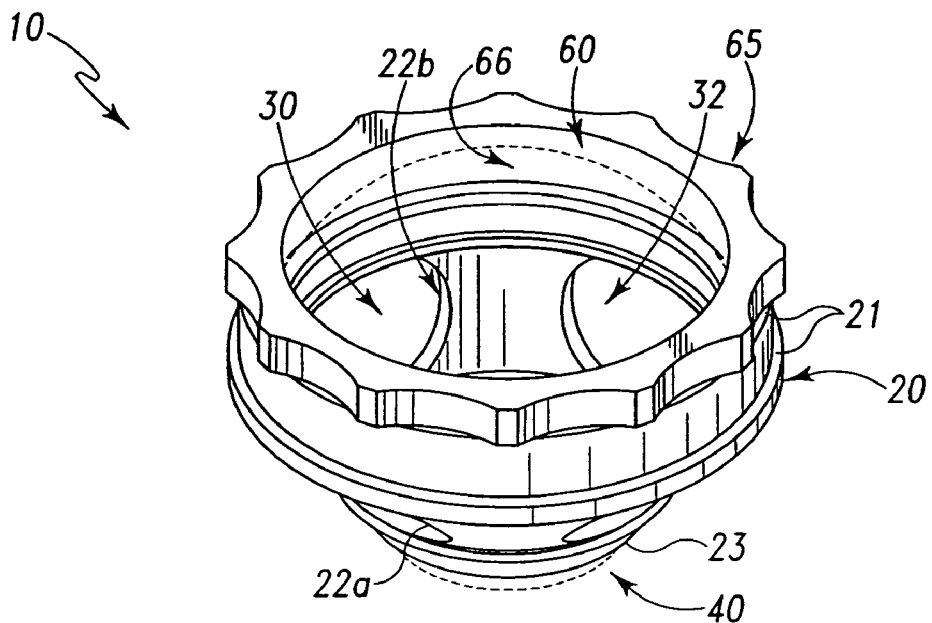
FIG. 1 is a top perspective view of an exemplary embodiment of an ophthalmoscopy lens system according to the present invention.
Figure 2:
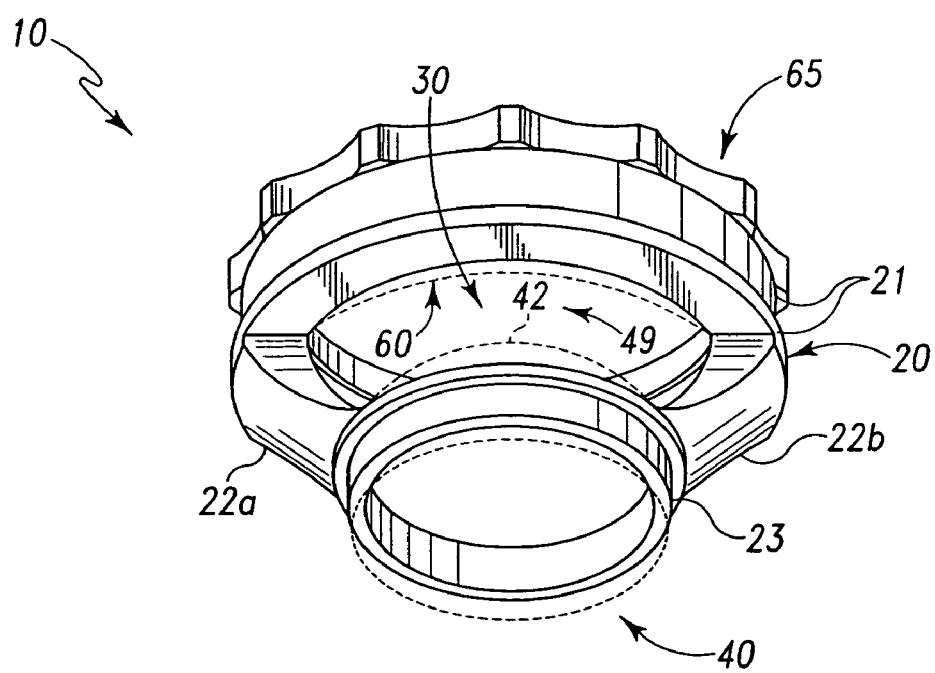
FIG. 2 is a bottom perspective view of an exemplary embodiment of the ophthalmoscopy lens system of FIG. 1.
Figure 3:
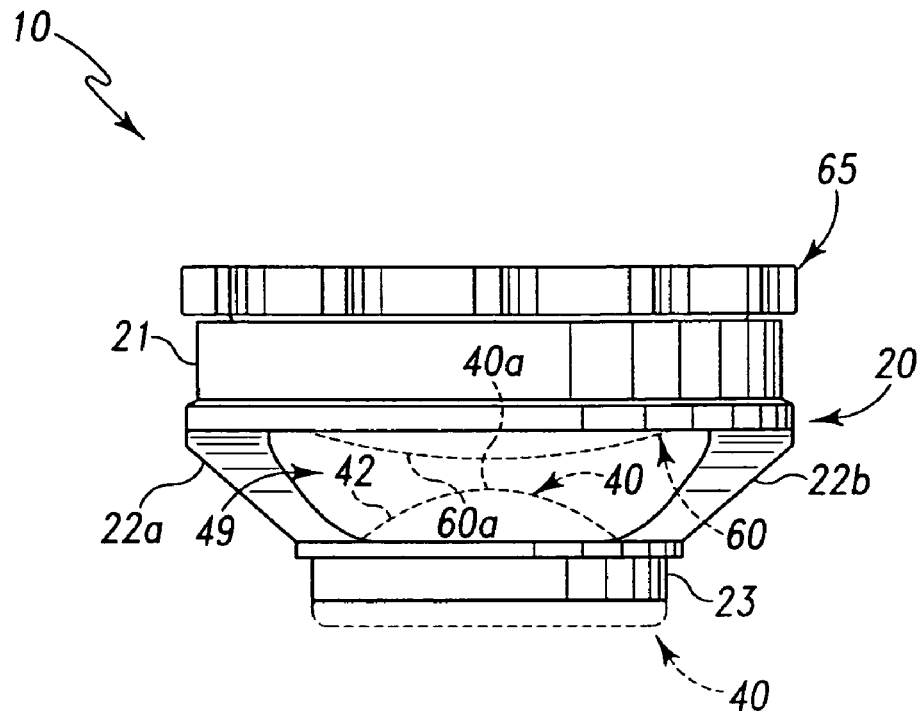
FIG. 3 is a front view of an exemplary embodiment of the ophthalmoscopy lens system of FIG. 1.
Figure 4:
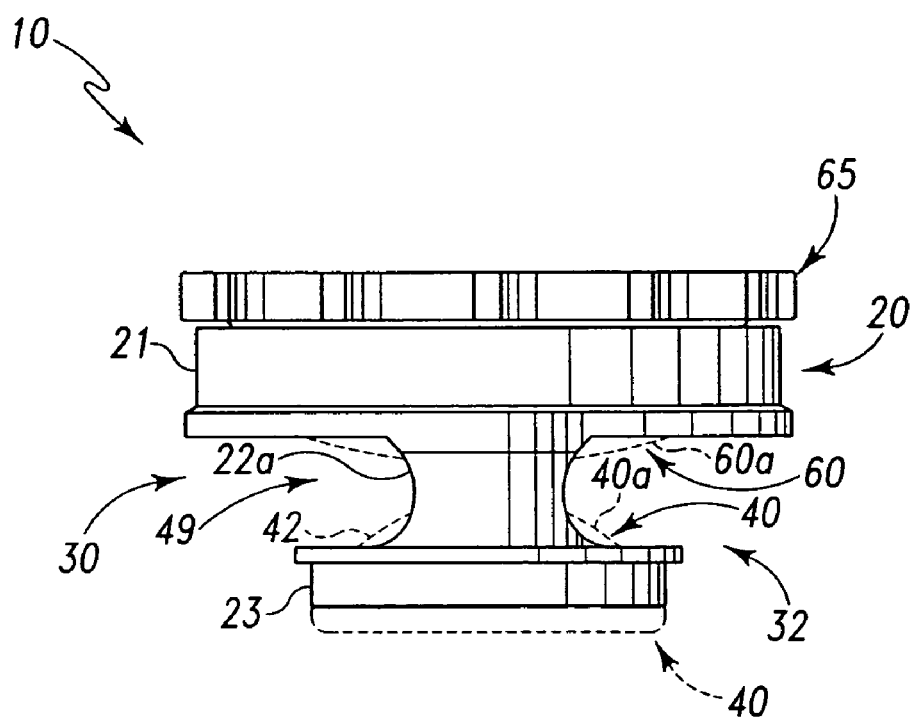
FIG. 4 is a side view of an exemplary embodiment of the ophthalmoscopy lens system of FIG. 1.
Figure 5:
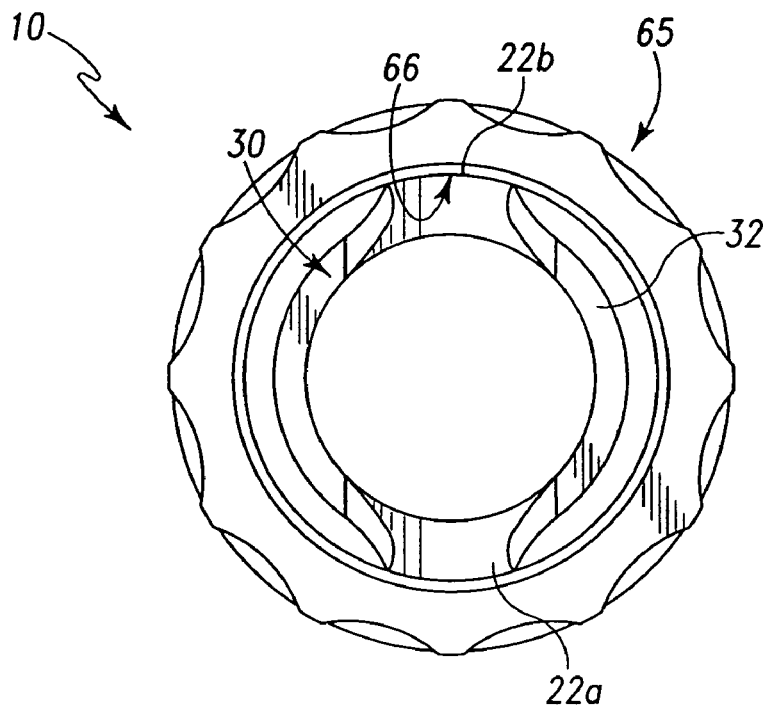
FIG. 5 is a top view of an exemplary embodiment of the ophthalmoscopy lens system of FIG. 1.
Figure 6:
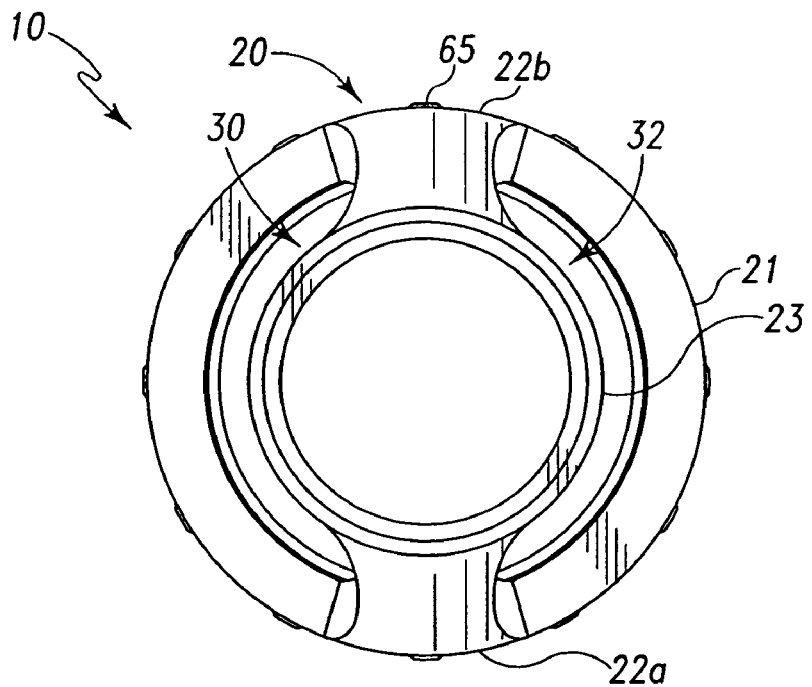
FIG. 6 is a bottom view of an exemplary embodiment of the ophthalmoscopy lens system of FIG. 1.

FIGS. 1 and 2 are top and bottom perspective views of a vitreoretinal lens system 10 according to one embodiment. Lens system 10 generally includes a contact lens element 40, an image forming lens 60, a retaining ring 65 and a housing or frame 20. As further described herein, contact lens element 40 may be secured to housing 20, while image forming lens 60 may be secured within retaining ring 65, which is then secured to housing 20.

As illustrated in FIGS. 1-8, housing 20 may be configured such that contact lens element 40 and retaining ring 65 (including image forming lens 60) may be mounted thereto in a predetermined, precise orientation, with an open air space 49 (best seen in FIG. 3) provided between contact lens element 40 and image forming lens 60. As discussed later herein, access to the open air space 49 between the contact and forming lenses, 40 and 60, can be provided through openings 30 and 32 in the housing 20.

Another aspect of the present invention is the selection of the materials for the individual components of the lens system in order to ensure that such materials are chemically, thermally and mechanically compatible with one another, as well as being impervious to common sterilants (such as bleach). Since imaging forming lens 60 will typically be made from glass, the type of glass used should not only provide the desired optical properties but also be suitable for sterilization.

U.S. patent application Ser. No. 11/391,922, titled Optimized Lens for Indirect Ophthalmoscopy hereby incorporated by reference describes glass formulations and compositions that can be used with the system described herein. For example, the image forming lens may include one that comprises a high index-of-refraction ($\geq 1.7$) optical glass composition meeting the following parameters:

% $SiO_2$ (by weight)+% $B_2O_3$ is less than 50% of the total weight of the composition;

the sum of the % of alkali metal compounds and the % of alkaline earth metal compounds is less than 10% of the total weight of the composition; and (% $SiO_2$+% $B_2O_3$)/(% rare earth compounds) is less than 1.

Of course, other compositions may be suitable for the image forming lens.

In addition, the glass may be chosen such that it may be sterilized in a solution of NaOH having a concentration of 1M NaOH and/or in a chlorine bleach solution (sodium hypochlorite) having a concentration of at least 20,000 ppm of free available chlorine (and perhaps even as high as 50,000 ppm, the equivalent of full strength household bleach). The glass may also be capable of being steam sterilized (e.g., in an autoclave) at temperatures of at least about 275° F. Of course, the lens systems may also be capable of being sterilized by other conventional means such as glutaraldehyde or hydrogen peroxide without damage. The selection of the "prescription" (or shape) of imaging forming lens 60 is well-known to those skilled in the art, and may be varied in order to provide the desired optical characteristics for lens system 10.

Figure 7:
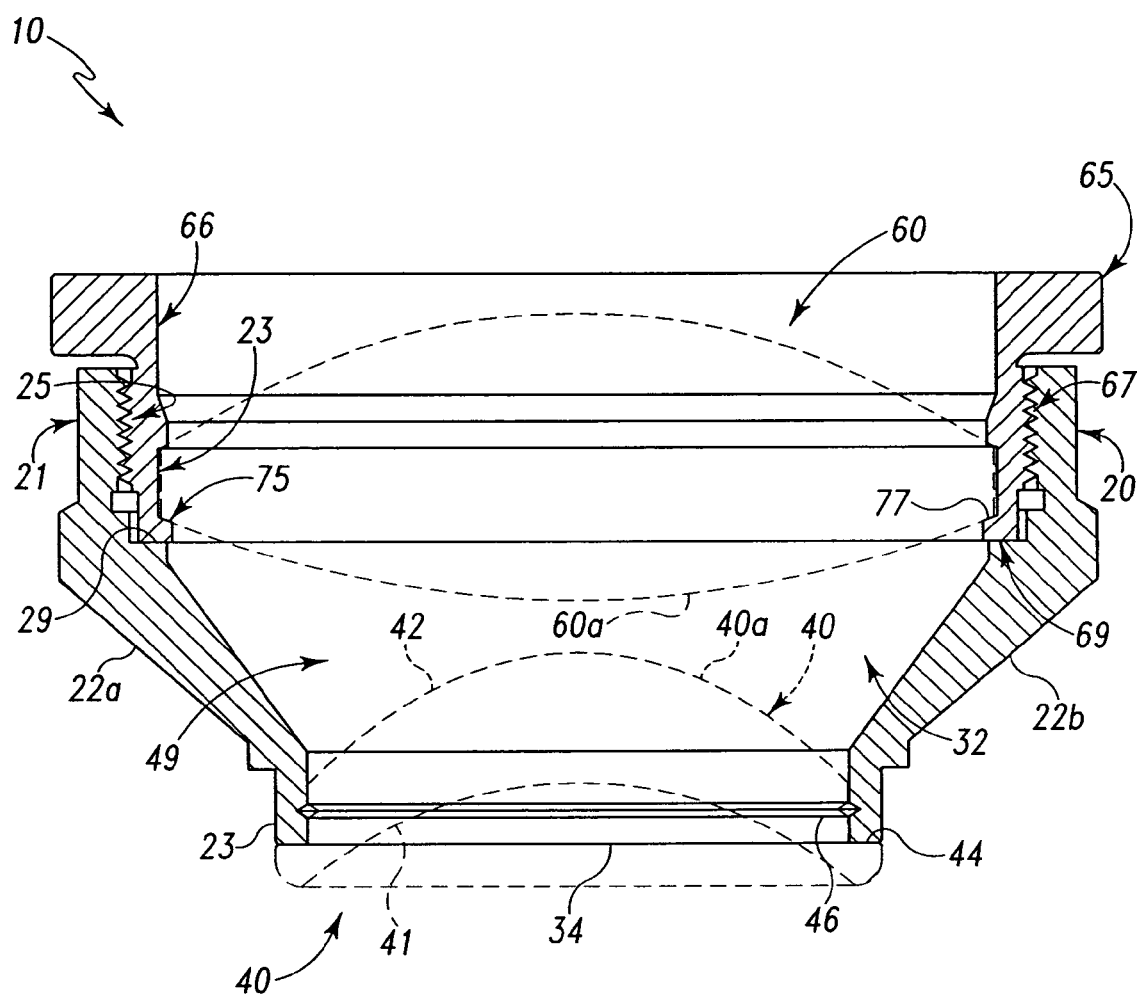
FIG. 7 is a cross-section view of an exemplary embodiment of the ophthalmoscopy lens system of FIG. 1.
Figure 8:
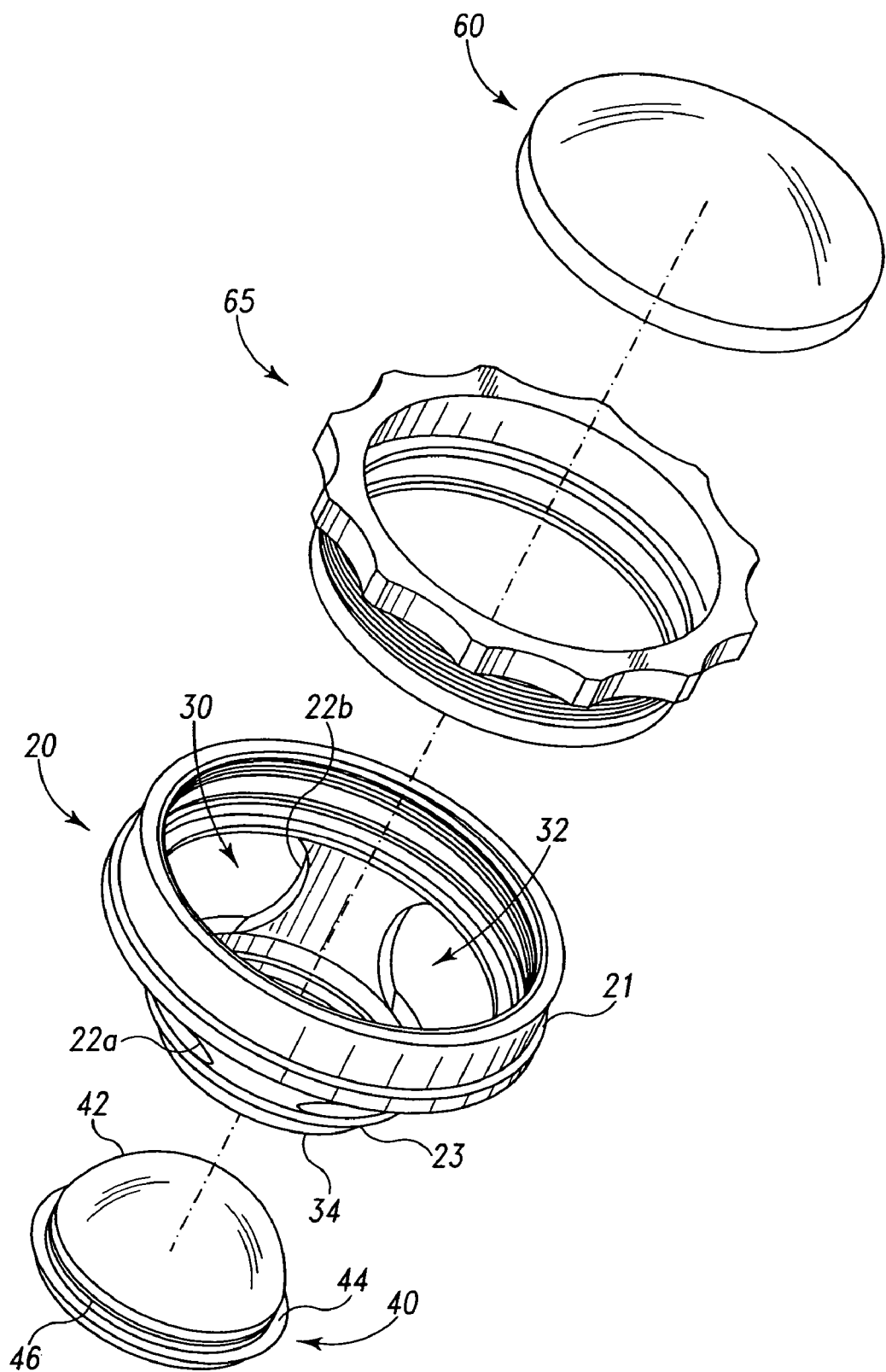
FIG. 8 is an exploded view of an exemplary embodiment of the ophthalmoscopy lens system of FIG. 1.

While contact lens element 40 may also be formed from glass, optical-grade plastic will more typically be used due to its ease of manufacture and its resistance to chipping. As best seen in FIG. 7, contact lens element 40 has a concave posterior surface 41 and a convex anterior surface 42. As used herein, the term "posterior" refers to the surface or part of a lens element which is located nearer to the patient's eye during normal use. Concave posterior surface 41 has a shape substantially corresponding to the shape of an average cornea. By way of example, concave posterior surface 41 may be spherical in shape and have an apical radius of approximately 7.5 to 8.0 mm. Convex anterior surface 42 may have a similar shape, or may be varied depending on the intended use of the lens, as is well-known to those skilled in the art. It will be understood that the shape of the surfaces of the contact lens element may be varied from that shown in order to provide the desired optical performance. The contact lens element may even include a flange, as well as suitable openings in the flange to accommodate surgical tools or instruments, as described in U.S. Pat. No. 5,963,301 (which is incorporated herein by reference). Such a lens system is particularly useful for vitreoretinal surgery. A compound contact lens element may also be employed, as described, for example, in U.S. Pat. No. 5,523,810 (which is incorporated herein by reference).

Likewise, the image forming lens element may be configured to provide any desired optical performance and characteristics. In particular, the lens systems shown in FIGS. 1-8 may be particularly useful as indirect ophthalmoscopy lenses. For example, the lens systems of U.S. Pat. No. 5,046,836 (which is incorporated herein by reference) may be readily modified in accordance with the teachings herein in order to provide a sterilizable and auto-clavable lens system. The image forming lens also may be specifically configured for optimal viewing of certain structures or portions of the eye (e.g., the fundus).

The material used in the manufacture of contact lens element 40 is chosen not only for its appropriate optical properties, but also to ensure that it is chemically resistant, particularly to sterilants such as bleach (e.g., sodium hypochlorite). In one embodiment, the plastic used to manufacture contact lens element 40, as well as the other materials used in the manufacture of the lens system, should be "sterilent-resistant." As used herein, the term "sterilent-resistant" means that the component may be sterilized in a chlorine bleach solution (sodium hypochlorite) having a concentration of at least 20,000 ppm of free available chlorine (and perhaps even as high as 50,000 ppm, the equivalent of full strength household bleach), without damage which affects the performance of the component. The components may also be "autoclavable", which means that the component can be steam sterilized (e.g., in an autoclave) at temperatures of at least about 275° F. (or even 300° F.) without damage which affects the performance of the component. It is also desired that the components may be sterilized in a solution of NaOH having a concentration of 1M NaOH without damage which affects the performance of the component.

Various sterilent-resistant and autoclavable plastics (high temperature plastics) may be used in the manufacture of contact lens element 40, particularly high temperature, chemically-resistant plastics having an index of refraction greater than about 1.4. Suitable plastics include: Ultem® 1010, an amorphous thermoplastic polyetherimide available from GE Plastics; Zeonor®, a cyclo-olefin polymer available from Zeon Corp.; Udel® P-3703 NT 05, a high temperature polysulfone available from Solvay Advanced Polymers; THV 220G, an optical-grade fluorinated terpolymer available from Dyneon; and NightShield®, a polyurethane available from Korry Electronics. During the manufacture of the contact lens element, as well as the frame and retaining ring (when made of plastic), the component should be annealed after fabrication in accordance with the annealing instructions provided by the manufacturer of the plastic.

Referring again to the drawings, housing or frame 20 and retaining ring 65 may also be made from a variety of materials which are sterilent-resistant. Most metals such as aluminum should be avoided, as they may corrode in a bleach solution. One particular material which may be employed is polyphenylsulfone thermoplastic resin which provides chemical resistance as well as heat resistance. Such materials are not only resistant to common sterilants (including bleach), they can also be heated to at least 275° F. without significant deformation (i.e., they are autoclavable). One particular polyphenylsulfone which may be used is medical-grade Radel®, a high performance polysulfone thermoplastic available from Solvay Advanced Polymers.

Turning to the specific structural aspects of the exemplary embodiment illustrated in FIGS. 1-8, housing or frame 20 may comprise an anterior portion 21 and a posterior portion 23 connected with two or more arms 22a and 22b. Generally, posterior portion 23 of housing 20 may be configured to receive or house the contact lens element 40 whereas anterior portion 21 may be configured to receive or house a retaining ring 65 having the image forming lens 60. Arms 22a and 22b may extend downward and inward from anterior portion 21 toward the posterior portion 23. In the embodiment illustrated in the figures, arms 22a and 22b provide a tapered transition between posterior portion 23 and anterior portion 21. In another embodiment, arms may comprise another arrangement to link the anterior and posterior portions. In addition, housing 20 may generally be symmetrically configured with respect to an optical axis OA (see FIG. 8).

Openings 30 and 32 are provided between arms 22a and 22b and anterior and posterior portions 21 and 23, and expose the inner surfaces of lenses 40 and 60. As set forth herein, openings 30 and 32 may be useful to expose the inner surfaces 40a and 60a, respectively, of contact and image forming lenses 40 and 60, so as to facilitate cleaning and sterilization of both surfaces of these lenses (e.g. inner and outer surface of each lens), as well as to facilitate drying thereof. Of course, a number of other arrangements configured to provide exposure to the contact 40 and image forming 60 lenses may be utilized. For example, many dimensions and styles of openings and arms may be incorporated in frame 20 so as to provide an air space 49 and exposure to the lenses. The arrangement shown is one exemplary, aesthetically pleasing configuration. It should be appreciated from the figures that arms 30 and 32 may be configured such that the openings defining the open air space extend about 50% or more of the circumference of the frame 20 between the anterior portion 21 and posterior portion 23. In addition, openings may extend about 50% or more of the circumference of the housing 20 between the adjacent arms 22a and 22b. Wherein a single arm is utilized, the openings defining the open air space may extend about 50% of a circumference of the frame 20 from a first side of the arm to a second side of the arm. The openings may even extend about 75% or more of the circumference discussed above to provide access to inner surfaces of contact and image forming lenses.

It should be understood that anterior portion 21 of frame should be of a sufficient diameter to receive and house a portion of retaining ring 65 therein. Still generally referring to FIGS. 1-8, retaining ring 65 may comprise a central opening 66 configured to secure image forming lens 60 therein for positioning within anterior portion 21 of housing 20 such that lens 60 is located in a predetermined, spaced-apart relationship with respect to contact lens element 40. More particularly, as best seen in FIG. 7, a groove 73 including a lower lip 75 may be provided along the inner surface of retaining ring 65. Lip 75 may provide a seating surface 77 for positioning image forming lens 60. In one embodiment, lens element 60 may be permanently attached within retaining ring 65 through a press fit or other conventional method. Where the press fitting method is used, image forming lens may be pressed within groove 73 or retaining ring 65 and seated against lip 75. Of course, it should be understood that any arrangement to permanently or temporarily secure lens element 60 within retaining ring 65 or frame 20 may be used. For example, in another embodiment, lens element 60 may be provided within an annular groove of frame 20 and secured within frame by a retaining ring (e.g., a ring that prevents vertical movement of the lens out of the frame 20).

With regard to securing the retaining ring 65 to the frame 20, as best seen in FIG. 7, the interior of the anterior portion 21 of frame 20 may comprise a plurality of threads 25 configured for mating engagement with threads 67 on retaining ring 65. In such embodiment, the retaining ring 65 may be secured to the frame 20 by aligning and screwing the threads 25 and 67 together until bottom surface 69 of retaining ring 65 abuts annular rim 29 of frame. Accordingly, in this exemplary embodiment, the retaining ring 65 may be removably secured partially within frame 20. In another embodiment, any arrangement to permanently or temporarily secure retaining ring 65 within frame 20 may be used.

As illustrated in FIGS. 1-8, contact lens element lens 40 includes a concave posterior surface 41 and a convex anterior surface 42 (also referenced as inner surface 40a). In order to facilitate positioning of lens 40 within frame 20, an annular lens wall 44 and annular contact groove 46 may extend about the circumference of the contact lens element 40 (best seen in FIGS. 7 and 8). The diameter of annular lens wall 44 may be substantially the same as that of outer diameter of frame annular surface 34 of posterior portion 23 of frame 20. In this manner, a flat surface will be provided such that, when contact lens element 40 is secured into frame 20, wall 44 will engage the annular surface 34. The engagement between wall 44 and annular surface 34 of frame 20 also serves to define the positioning of contact lens 40 in frame 20. In other words, contact lens 40 may be inserted into frame 20 until the engagement of wall 44 with surface 34 limits further penetration of contact lens element 40 into frame 20. This ensures that the desired spacing between contact lens element 40 and image forming lens 60 is maintained.

In one embodiment, contact lens element 40 may be secured within frame 20 by applying a glue within an annular contact groove 46 and positioning lens element 40 within the posterior portion of the frame until the engagement of wall 44 with surface 34 limits further penetration of contact lens element 40. In another embodiment, lens element 40 and interior of posterior portion 23 may comprise complimentary threads, similar to that of the retaining ring 65 and anterior portion 21 so that contact lens element 40 may be threadingly secured to the frame. Of course, any arrangement to permanently or temporarily secure the contact lens element 40 within frame 20 may be used.

It should be understood that the exemplary lens systems described above and shown in FIGS. 1-8 may be configured in a variety of arrangements. Essentially, any multi-element ophthalmoscopy lens system in which air separates at least two of the lens elements may be configured in the manner described previously. Thus, multiple image forming lens elements may be included, as desired or necessary, and each of the lens elements may be mounted to the housing in any of the manners described above.

In addition, removability of the retaining ring/image forming lens facilitates the cleaning the internal contact element and image forming lens surfaces of any surgical debris or, alternatively, autoclave surface depositions that might not be easily cleaned via the openings in the housing that are advantageously provided.

The foregoing description of the various embodiments has been presented for the purposes of illustration and description. It is not intended to be exhaustive or to limit the invention to the precise form disclosed. Many alternatives, modifications and variations will be apparent to those skilled in the art of the above teaching. For example, the lens systems in accordance with the present invention may comprise a variety of arrangements such that an open air space exists between the contact and image forming lenses. Accordingly, while some of the alternative embodiments of the lens systems have been discussed specifically, other embodiments will be apparent or relatively easily developed by those of ordinary skill in the art.

What is claimed is:

1. An ophthalmoscopy lens system comprising a contact lens and an image forming lens each of said contact and image forming lenses having an inner surface, with the inner surface of the contact lens facing the inner surface of the image forming lens, wherein said contact lens and said image forming lens are held in a spaced-apart arrangement within a frame such that an open air space is provided between said contact lens and said image forming lens and said inner surfaces are exposed to open air.

2. The ophthalmoscopy lens system of claim 1, further comprising a retaining ring for retaining said image forming lens in said frame.

3. The ophthalmoscopy lens system of claim 2, wherein said retaining ring is removably secured to said frame.

4. The ophthalmoscopy lens system of claim 3, wherein said image forming lens is held within said retaining ring.

5. The ophthalmoscopy lens system of claim 1, wherein said frame comprises anterior and posterior portions and an arm connecting said anterior and posterior portions.

6. The ophthalmoscopy lens system of claim 5, further comprising openings between said anterior and posterior portions which expose said air space.

7. The ophthalmoscopy lens system of claim 6, wherein said openings extend greater than 50% of a circumference of the frame between said anterior portion and said posterior portion.

8. The ophthalmoscopy lens system of claim 6, wherein said openings extend greater than 50% of a circumference of the frame from a first side of said arm to a second side of said arm.

9. The ophthalmoscopy lens system of claim 1, wherein said contact lens is removably secured to said frame.

10. The ophthalmoscopy lens system of claim 2, wherein said retaining ring is mounted to an anterior portion of said frame and said contact lens is secured to a posterior portion of said frame.

11. The ophthalmoscopy lens system of claim 1, wherein said contact lens has a concave posterior surface and a convex anterior surface.

12. The ophthalmoscopy lens system of claim 1, wherein said contact and image forming lenses are symmetrically configured with respect to an optical axis.

13. The ophthalmoscopy lens system of claim 1, wherein said imaging forming lens is fabricated using a glass material having the following compositional properties:

$\%$ $SiO_2$ (by weight)+% $B_2O_3$ is less than 50% of the total weight of the composition;

the sum of the % of alkali metal compounds and the % of alkaline earth metal compounds is less than 10% of the total weight of the composition; and (% $SiO_2$+% $B_2O_3$)/(% rare earth compounds) is less than 1.

14. An ophthalmoscopy lens system comprising:

a frame having anterior and posterior portions, said frame housing a contact lens secured to said posterior portion of said frame, said contact lens including an inner anterior surface; and a retaining ring removably secured to said anterior portion of said frame, said retaining ring for retaining an image forming lens including an inner posterior surface, wherein said contact lens and said image forming lens are in a spaced-apart arrangement such that an open air space exists between said contact lens and said image forming lens and said inner surfaces are exposed to open air.

15. The ophthalmoscopy lens system of claim 14, further comprising an arm connecting said anterior and posterior portions and openings between said anterior and posterior portions through which said inner surfaces are exposed.

16. The ophthalmoscopy lens system of claim 15, wherein said openings extend greater than 50% of a circumference of the frame between said anterior portion and said posterior portion.

17. The ophthalmoscopy lens system of claim 15, wherein said openings extend greater than 50% of a circumference of the frame from a first side of said arm to a second side of said arm.

18. The ophthalmoscopy lens system of claim 14, wherein said contact lens is a compound contact lens.

19. The ophthalmoscopy lens system of claim 18, wherein said imaging forming lens is fabricated using a glass material having the following compositional properties:
%  $SiO_2$ (by weight)+%  $B_2O_3$ is less than 50% of the total weight of the composition;
the sum of the % of alkali metal compounds and the % of alkaline earth metal compounds is less than 10% of the total weight of the composition; and
(%  $SiO_2$+%  $B_2O_3$)/(% rare earth compounds) is less than 1.

20. The ophthalmoscopy lens system of claim 14, wherein said image forming lens is held within said retaining ring.

* * * * *